United States Patent
Graupner et al.

(10) Patent No.: US 8,187,536 B2
(45) Date of Patent: May 29, 2012

(54) SYSTEM AND METHOD FOR THE UNEQUIVOCAL ALLOCATION OF HISTOLOGICAL CASSETTES AND SPECIMEN SLIDES

(75) Inventors: Dag Graupner, Eppelheim (DE); Rolf Metzner, Dossenheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 12/959,755

(22) Filed: Dec. 3, 2010

(65) Prior Publication Data

US 2011/0114719 A1 May 19, 2011

Related U.S. Application Data

(62) Division of application No. 10/936,893, filed on Sep. 9, 2004, now Pat. No. 7,867,442.

(30) Foreign Application Priority Data

Sep. 12, 2003 (DE) .................................. 103 42 264

(51) Int. Cl.
*G01N 21/00* (2006.01)
(52) U.S. Cl. ................ 422/63; 422/64; 422/65; 422/67; 435/287.1; 436/46; 436/47; 436/180
(58) Field of Classification Search .............. 422/63–65, 422/67; 435/287.1; 436/46–47, 180
See application file for complete search history.

(56) References Cited

U.S. PATENT DOCUMENTS

| 5,690,892 A | 11/1997 | Babler et al. |
| 2002/0018733 A1 | 2/2002 | Kapplein et al. |
| 2004/0253662 A1 | 12/2004 | Heid et al. |

FOREIGN PATENT DOCUMENTS

| DE | 10154843 A1 | 5/2003 |
| EP | 1154301 A1 | 11/2001 |
| JP | 2001-306692 A | 11/2001 |
| JP | 2001-180662 A | 7/2003 |
| WO | 00/62035 | 10/2000 |
| WO | 03/040694 A1 | 5/2003 |

*Primary Examiner* — Jyoti Nagpaul
(74) *Attorney, Agent, or Firm* — Hodgson Russ LLP

(57) ABSTRACT

A system (100) and a method for the unequivocal allocation of histological cassettes (30) and specimen slides (60) is described. The system encompasses a microtome (1) and at least one reading unit (80). The data (33) of the histological cassette (30) and the data (33) of the at least one specimen slide (60) are read by means of the reading unit (80). The reading unit (80) is provided with at least one indicating element (83) that outputs a signal in accordance with the degree of correspondence between the data (33) of the histological cassette (30) and the data (33) on the specimen slide (60).

17 Claims, 5 Drawing Sheets

SYSTEM AND METHOD FOR THE UNEQUIVOCAL ALLOCATION OF HISTOLOGICAL CASSETTES AND SPECIMEN SLIDES

This application is a divisional of U.S. patent application Ser. No. 10/936,893 now U.S. Pat. No. 7,867,442, filed Sep. 9, 2004, which in turn claims priority of the German patent application 103 42 264.0 filed on Sep. 12, 2003, the disclosures of which are incorporated by reference herein.

FIELD OF THE INVENTION

The invention concerns a system for the unequivocal allocation of histological cassettes and specimen slides.

The invention further concerns a method for the unequivocal allocation of histological cassettes and specimen slides.

BACKGROUND OF THE INVENTION

German Unexamined Application DE 101 54 843 discloses a method and an apparatus for labeling specimen slides for microtomed tissue samples. The data applied onto the histological cassettes are sensed upon insertion into the microtome. Associated with the microtome is a printer to which the data read in the microtome are transferred. Only those specimen slides that correspond to the tissue sample clamped in the microtome are then printed.

SUMMARY OF THE INVENTION

It is the object of the invention to create a system that enables dependable and unmistakable allocation of thin sections to preprinted specimen slides The aforesaid object is achieved by way of a system for the unequivocal allocation of histological cassettes and specimen slides, the system comprising a microtome, at least one reading unit that reads data of the histological cassette and data of the at least one specimen slide, wherein the histological cassette and the specimen slide is associated with the microtome; and at least one indicating element associated with the reading unit, wherein the reading unit outputs a signal in accordance with the degree of correspondence between the data of the histological cassette and the data on the specimen slide.

A further object of the invention to create a method that enables dependable, unmistakable allocation of thin sections to preprinted specimen slides The aforesaid object is achieved by way of a method for the unequivocal allocation of histological cassettes and specimen slides, comprising the following steps:

reading data using at least one reading unit, the data being allocated to the histological cassette and the specimen slides;

comparing the data read from the histological cassette with the data read from the specimen slides; and outputting, by means of an indicating element, a signal that indicates the degree of correspondence between the data of the histological cassette and the data on the specimen slide.

The advantage of the present invention is that the system is suitable for the unequivocal allocation of histological cassettes and specimen slides. The system encompasses a microtome and at least one reading unit that reads the data of the histological cassette and data of the at least one specimen slide, and that the reading unit is provided with at least one indicating element that outputs a signal in accordance with the degree of correspondence between the data of the histological cassette and the data on the specimen slide.

The data are applied onto the histological cassette and the specimen slides in an extra printer. As a rule, for each histological cassette one to five specimen slides are printed with the same data as the histological cassette.

Data on the specimen slide and on the histological cassette can be applied in any form. The forms can also be mixed with one another. It is thus possible to apply only a barcode, only readable written characters, or a mixture of barcode and readable written characters onto the specimen slide or the histological cassette.

An additional advantage exists when a data connection is provided between the microtome and the reading unit. Operation of the microtome is then, furthermore, blocked in the event of lack of correspondence between the data on the histological cassette and the specimen slide.

Further advantageous embodiments of the invention are evident from the dependent claims.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
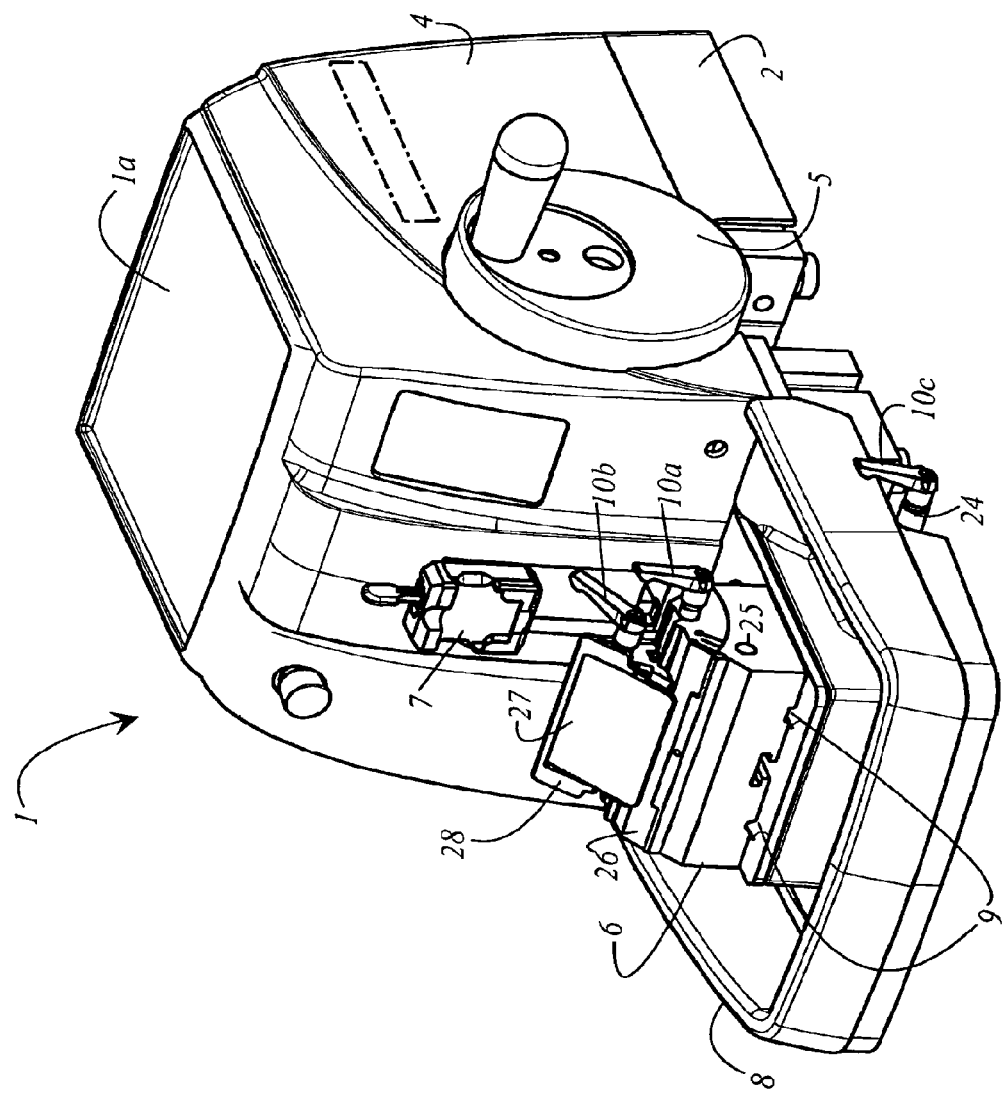
FIG. 1 is a perspective view of the rotary microtome having a reading unit arranged on the microtome housing.

FIG. 1 is a perspective view of rotary microtome 1. Rotary microtome 1 comprises substantially a base part 2 and a microtome housing 4 provided on the base part. A knife holder 6 is placed on base part 2. Provided opposite knife holder 6 on microtome housing 4 is a sample holder 7 that can be moved up and down by means of a handwheel 5 provided on microtome housing 4.

Histological cassettes 30 (see FIG. 4a) can be clamped in sample holder 7. Cover 31 is removed from histological cassettes 30 so that a sample 41 embedded in paraffin wax 40 can be cut by means of the microtome. Knife holder 6 and sample holder 7 are arranged opposite one another. Provided on base part 2 are two rail elements 9 on which knife holder 6 can be adjusted in terms of its distance with respect to sample holder 7. Knife holder 6 is surrounded by a pan 8. Pan 8 is U-shaped and adjoins microtome housing 4 and base part 2 without a step. Arranged on knife holder 6 is a knife support element 26 that can be immobilized by means of a hex socket screw 25. Knife holder 6 has a convexly curved surface that coacts with a concavely curved surface on the knife support element. Knife holder 6 can be moved freely on the convexly curved surface of the knife support element, and every angular position is clamped in place with hex socket screw 25. This likewise makes possible free angular adjustment of a knife 27 provided on knife support element 26. A knife carriage 28 is provided on knife support element 26, a first clamping lever 10a mounted on knife support element 26 serving to clamp and immobilize knife carriage 28. A second clamping lever 10b that serves to clamp the knife is provided on knife carriage 28. A third clamping lever 10c is provided on a side wall of pan 8, and coacts via a mechanical coupling 24 with knife holder 6. By means of third clamping lever 10c, knife holder 6 is clamped with respect to base part 2.

Figure 2:
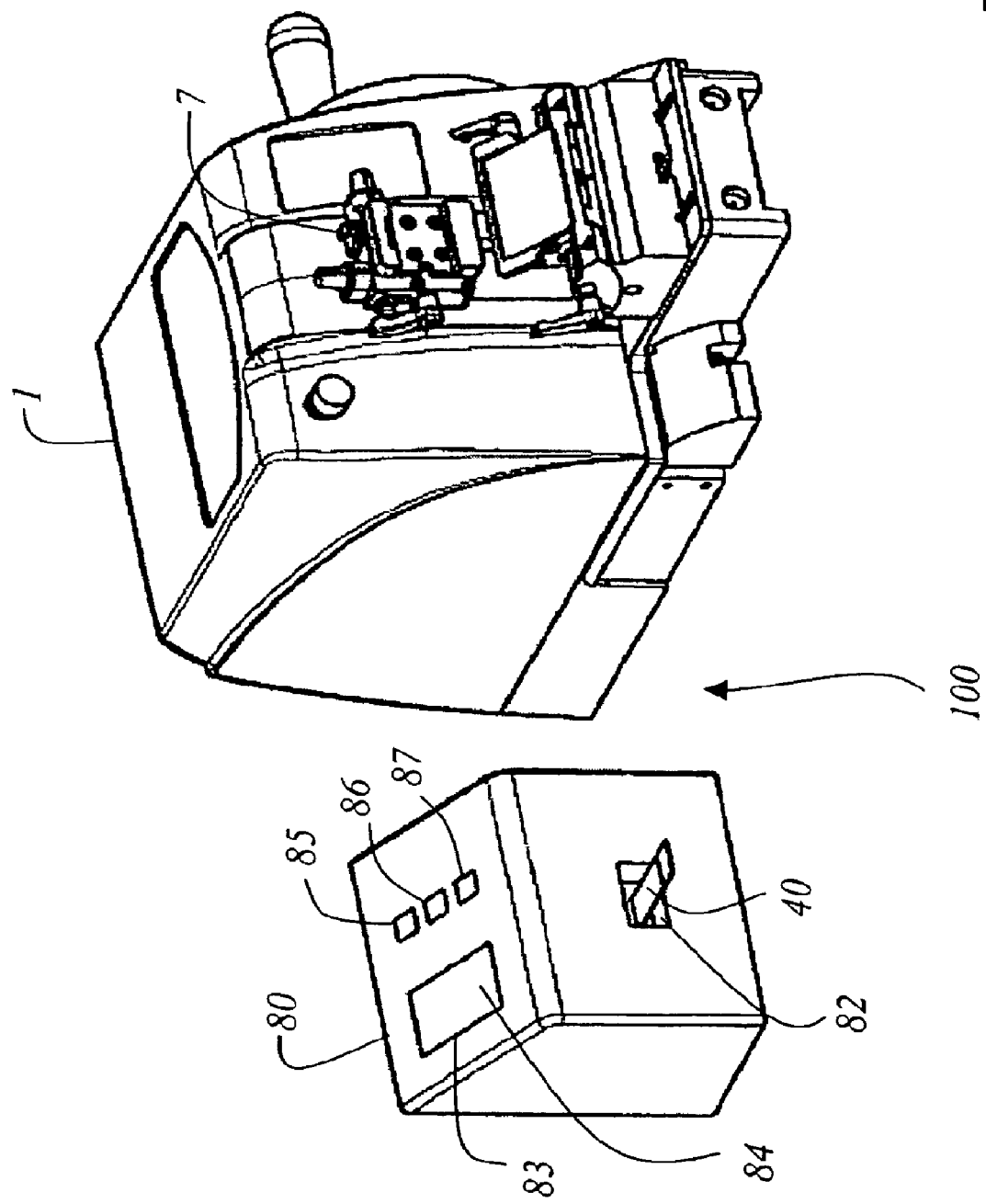
FIG. 2 schematically depicts a first embodiment of the system of microtome and reading unit.

FIG. 2 shows system 100 according to the present invention that is made up of microtome 1 and at least one reading unit 80. In this exemplary embodiment, reading unit 80 is separate from microtome 1. It is also conceivable for reading unit 80 to be mounted directly on microtome 1. In addition, a reading unit 80 could be integrated into sample holder 7. This reading unit would read exclusively the data that are printed onto histological cassette 30. A further reading unit 80 would be provided that reads exclusively data that are printed onto the specimen slide. The reading unit 80 can be embodied as a scanner, for example a barcode scanner, and preferably a scanner having both a barcode recognition system and a character recognition system built into it.

Figure 3:
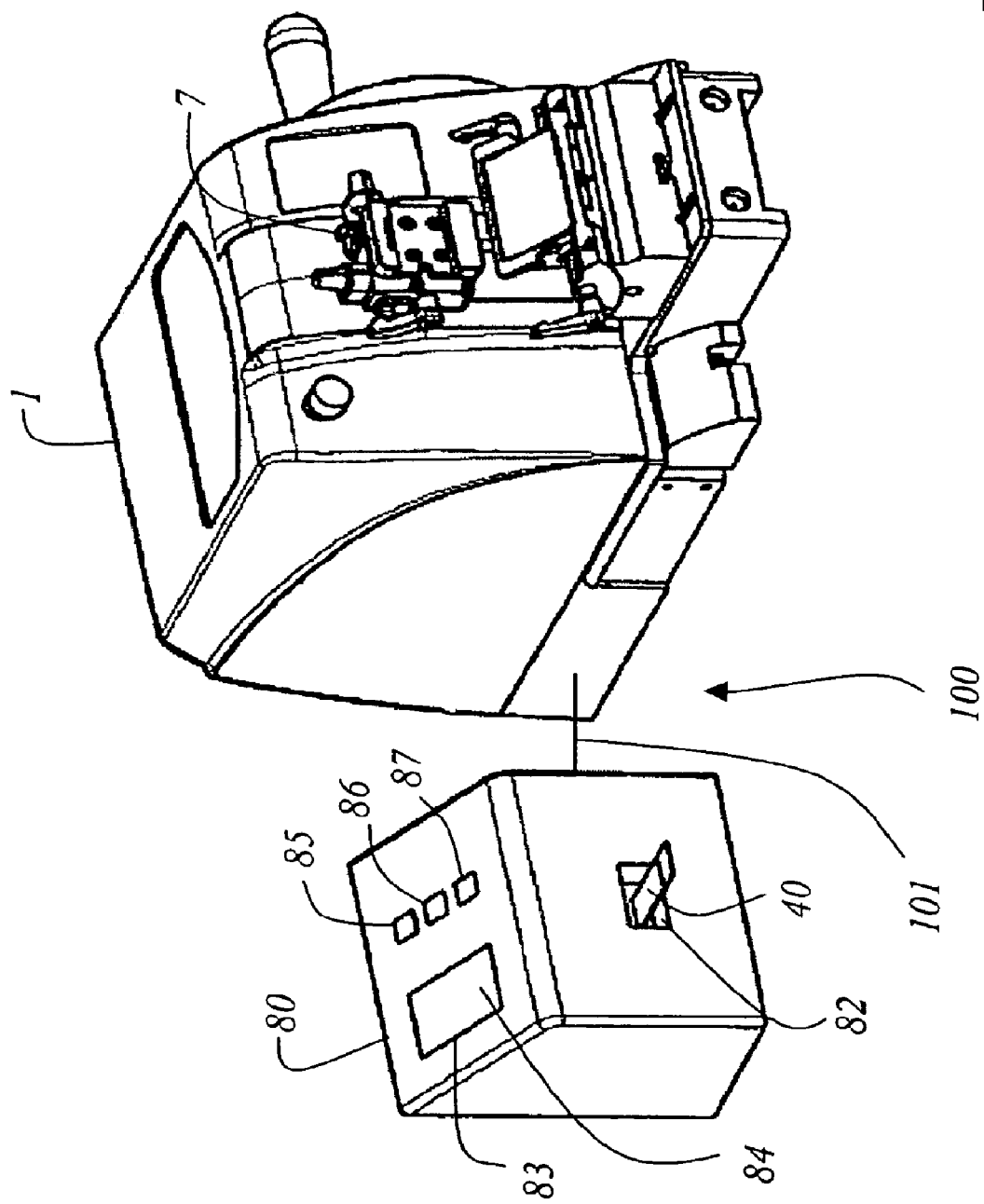
FIG. 3 schematically depicts a second embodiment of the system of microtome and reading unit.

Reading unit 80 can be connected to microtome 1 via a data connection 101 (see FIG. 3). Data connection 101 can be created by way of a conventional electrical conductor or a wireless connection.

Data 33 present on histological cassette 30 are read first at reading unit 80. Next to be read at the reading unit are data 33 of specimen slide 60, onto which thin sections 42, produced from samples 41 embedded in paraffin wax 40, are to be placed. As depicted in FIG. 2 and FIG. 3, reading unit 80 encompasses an opening 82 or a window in or on which are positioned data 33 to be read on specimen slide 60 or histological cassette 30. Reading unit 80 encompasses at least one indicating element 83 that is embodied as display 84 in the exemplary embodiment depicted here, or as colored light sources 85, 86, 87. On display 84, a text message can be outputted to the user if the data on histological cassette 30 and on one of the several specimen slides 40 do not correspond. A notification can likewise be outputted to the user if a visual comparison by him of the data on specimen slide 40 and/or histological cassette 30 is additionally necessary. The notification or signal of reading unit 80 can be acoustic and/or optical. Only those specimen slides 40 that exhibit a correspondence between the data on histological cassette 30 and on specimen slide 40 must be conveyed to microtome 1.

When colored light sources 85, 86, 87 are used as the indication for the user, a green light signal then, for example, indicates a correspondence between the data on histological cassette 30 and on specimen slide 4. With a red light signal, there is a lack of correspondence between the data on histological cassette 30 and on specimen slide 4. A yellow light signal indicates to the user that a visual comparison of the data on specimen slide 40 and/or histological cassettes 30 is necessary.

If, as depicted in FIG. 3, microtome 100 is connected to reading unit 80 via a data connection, the cutting process with the microtome can be stopped, for example, in the absence of a correspondence between the data on histological cassette 30 and on specimen slide 4. The cutting process is not continued until a correspondence exists between the data on histological cassette 30 and on specimen slide 4.

Figure 4A:
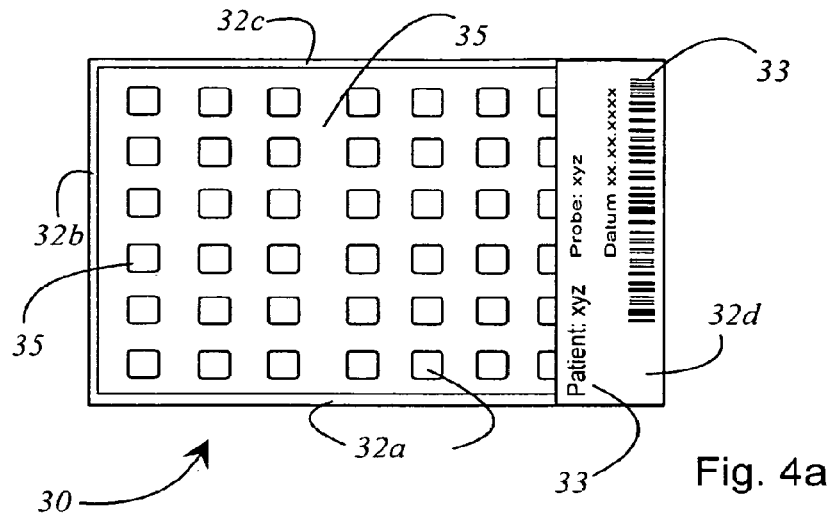
FIG. 4a is a view of a histological cassette with the data printed thereon.

FIG. 4a is a view of a histological cassette 30 with data 33 printed thereonto. Histological cassette 30 has a bottom 34 and a first, second, third, and fourth side wall 32a, 32b, 32c, and 32d. First, second, and third side walls 32a, 32b, and 32c are perpendicular to bottom 34. Fourth side wall 32a is inclined at an acute angle with respect to bottom 34. Bottom 34 possesses a plurality of openings 35 so that upon embedding of sample 41, the latter also has sufficient paraffin wax 40 flowing around it.

Figure 4B:
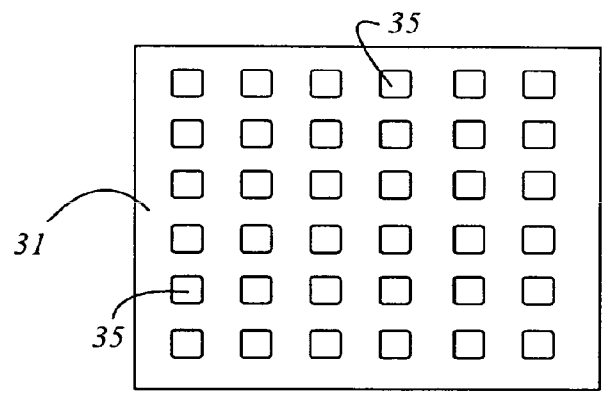
FIG. 4b is a view of a cover with which the histological cassette is closed off for embedding of the sample in paraffin wax.

FIG. 4b is a view of a cover 31 with which histological cassette 30 is closed off for the embedding of sample 41 in paraffin wax 40. The cover likewise encompasses openings 38 to ensure that paraffin wax 40 passes through. In addition, cover 31 prevents sample 41 from falling out during the embedding operation.

Figure 5:
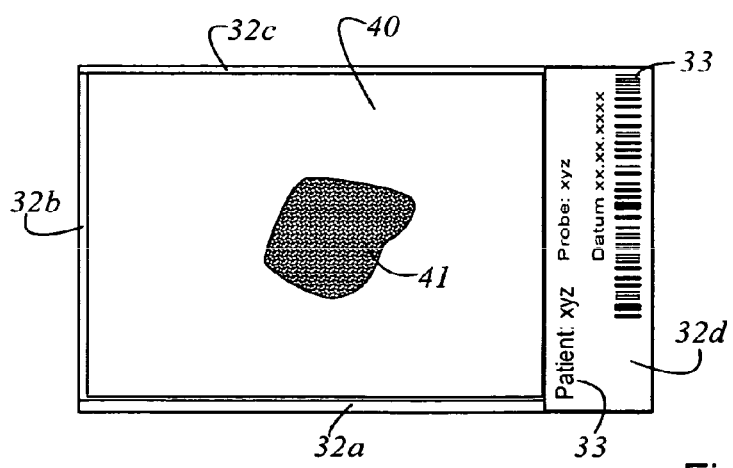
FIG. 5 is a view of a histological cassette in which a sample is embedded in paraffin wax.

FIG. 5 is a view of a histological cassette 30 in which sample 41 is embedded in paraffin wax 40. The cover is removed after paraffin wax 40 has solidified. The block of paraffin wax 40 and sample 41 embedded therein is located in a pan constituted by bottom 34 and the four side walls 32a, 32b, 32c, and 32d. Before sample 41 can be cut using microtome 1, the block of paraffin wax 40 is removed from the pan and mounted on the side of the bottom of the histological cassette that is located opposite the opening of the pan. Histological cassette 30 is then clamped into sample holder 7 of microtome 1.

Figure 6:
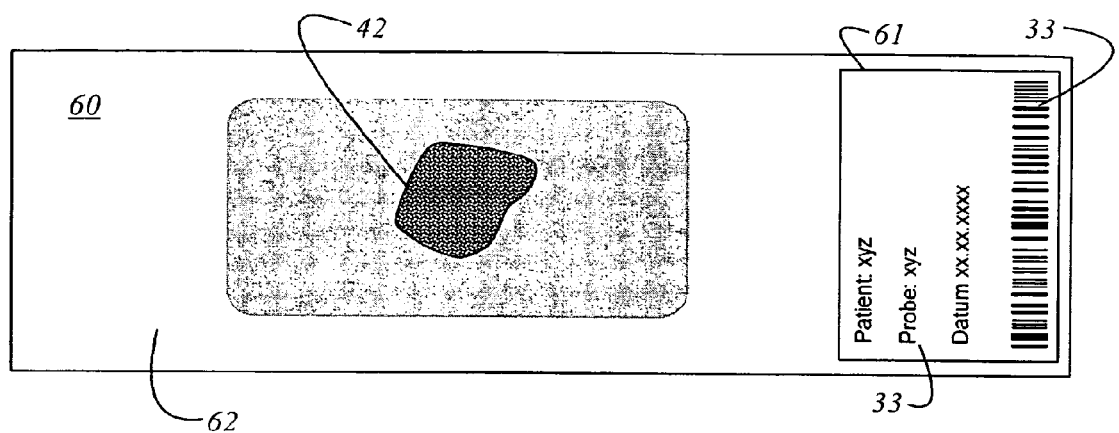
FIG. 6 is a view of a specimen slide with the data printed thereon.

FIG. 6 is a view of a specimen slide 60 with data 33 printed thereon. A field 61 is provided on specimen slide 60 for data 33. At least one thin section 42 of sample 41 is applied onto a transparent part 62 of the specimen slide.

The invention has been described with regard to the preferred exemplary embodiments. It is self-evident to one skilled in the art that changes and modifications can be made without leaving the range of protection of the claims below.

What is claimed is:

1. A method for the unequivocal allocation of a histological cassette with a specimen slide comprising the steps of:
    reading data using at least one reading unit, the data being provided on the histological cassette and on the specimen slide;
    comparing the data read from the histological cassette with the data read from the specimen slide; and
    outputting, by means of an indicating element, a signal that indicates a degree of correspondence between the data read from the histological cassette and the data read from the specimen slide.

2. The method as defined in claim 1, wherein the data on the histological cassette and on the specimen slide are printed on.

3. The method as defined in claim 2, wherein the data on the histological cassette and on the specimen slide are in the form of a barcode.

4. The method as defined in claim 2, wherein the data on the histological cassette and on the specimen slide are in the form of a barcode and readable characters.

5. The method as defined in claim 2, wherein the data on the histological cassette and on the specimen slide are in the form of readable characters.

6. The method as defined in claim 1, wherein the reading unit is a scanner; and
    the data on the histological cassette or on the specimen slide are presented to the scanner.

7. The method as defined in claim 1, wherein the indicating element is a display;
    and the signal is a datum regarding the correspondence between the data on the histological cassette and on the specimen slide.

8. The method as defined in claim 1, wherein the step of outputting a signal includes illuminating one of a first light source, a second light source, and a third light source, the first light source emitting green light, the second light source emitting yellow light, and the third light source emitting red light.

9. The method as defined in claim 1, wherein a data connection is provided between the microtome and the reading unit.

10. The method as defined in claim 9, further comprising the step of blocking operation of the microtome if the signal indicates lack of correspondence between the data on the histological cassette and the data on the specimen slide.

11. The method as defined in claim 1, further comprising the step of operating the microtome only if there is correspondence between the data on the histological cassette and the data on the specimen slide.

12. The method as defined in claim 1, wherein the signal is an optical signal.

13. The method as defined in claim 1, wherein the signal is an acoustic signal.

14. The method as defined in claim 1, wherein the signal is an acoustic and optical signal.

15. The method according to claim 1, wherein the degree of correspondence is chosen from a plurality of degrees including complete correspondence between the data read from the histological cassette and the data read from the specimen slide and lack of complete correspondence between the data read from the histological cassette and the data read from the specimen slide.

16. The method according to claim 15, wherein the plurality of degrees further includes a degree indicating a need for visual comparison of the data on the histological cassette with the data on the specimen slide.

17. A subsystem for the unequivocal allocation of a histological cassette carrying an embedded sample with at least one specimen slide intended to receive microtomed thin sections cut from the sample, the subsystem comprising:

a reading unit that reads data on the histological cassette and data on a specimen slide, wherein the reading unit compares the data read from the histological cassette with the data read from the specimen slide to determine if correspondence exists between the data on the histological cassette and the data on the specimen slide; and an indicating element associated with the reading unit for outputting a signal indicating if correspondence exists between the data on the histological cassette and the data on the specimen slide.

* * * * *